United States Patent [19]
Hsi

[11] Patent Number: 5,773,833
[45] Date of Patent: Jun. 30, 1998

[54] PHOTO-IONIZATION DETECTOR FOR VOLATILE GAS MEASUREMENT

[75] Inventor: Peter C. Hsi, Fremont, Calif.

[73] Assignee: RAE Systems, Inc., Sunnyvale, Calif.

[21] Appl. No.: 620,635

[22] Filed: Mar. 22, 1996

[51] Int. Cl.$^6$ .................................................. G01N 27/66
[52] U.S. Cl. ........................................ 250/382; 250/379
[58] Field of Search ................................. 250/372, 379, 250/382, 423 D

[56] References Cited

U.S. PATENT DOCUMENTS

| 2,959,677 | 11/1960 | Robinson et al. | 250/382 X |
|---|---|---|---|
| 4,778,998 | 10/1988 | Carnahan . | |
| 5,393,979 | 2/1995 | Hsi . | |
| 5,572,137 | 11/1996 | Jones | 250/382 X |

FOREIGN PATENT DOCUMENTS

| 9427141 | 11/1994 | WIPO | 250/382 |
|---|---|---|---|

*Primary Examiner*—Edward J. Glick
*Attorney, Agent, or Firm*—Skjerven, Morrill, MacPherson, Franklin & Friel LLP; David T. Millers

[57] ABSTRACT

A photo-ionization detector (PID) which measures volatile organic gas uses electrically insulated parallel plates to energize a miniaturized gas discharge UV lamp and an energy efficient method to modulate the UV lamp intensity and reduce power consumption. A miniaturized centrifugal pump is integrated into the PID to provide active sampling for fast response to volatile gas. An ionization chamber in the PID includes a UV shield which protects a measurement electrode from UV light and a UV monitor which measures changes in UV intensity due to external interferences and UV lamp variations. A microprocessor in the PID uses measurements from the measurement electrode and from the UV monitor to accurately account for UV intensity variations when determining a volatile gas concentration.

25 Claims, 5 Drawing Sheets

PHOTO-IONIZATION DETECTOR FOR VOLATILE GAS MEASUREMENT

BACKGROUND OF THE INVENTION

1. Field of the Invention

This invention relates to volatile gas detectors and particularly to a low power portable photo-ionization detector having a sampling pump and an ultraviolet light sensor within a housing that forms an ionization chamber.

2. Description of Related Art

Photo-ionization detectors (PIDs) can detect volatile organic gas. A typical PID includes a source of high energy photons, an ionization chamber, and an ion detector. A typical high energy photon source is a gas discharge ultraviolet (UV) lamp which produces high energy photons having energy of above about 9.2 electron-volt (eV). In a PID, high energy photons from the photon source are directed into the ionization chamber and may hit molecules having ionization potentials below the energies of the photons. Such collisions ionize molecules so that the molecules are electrically detectable as ions and electrons.

A conventional gas discharge UV lamp for a PID is a sealed glass envelope containing two plates. A high voltage which is applied to the plates via the leads that extend from the plates out of the glass envelope causes a glow discharge process in a gas which is trapped in the envelope. The glow discharge process generates UV photons which exit the envelope through an optical window and illuminate the ionization chamber of the PID. A problem with existing UV lamps is that they are relatively large (at least 0.5 inch in diameter and 2 inch in length) and consume a relatively large amount of energy (typically 1 watt or more). This makes miniaturization of PIDs for portable use such as for a battery powered pocket size gas monitor difficult because the lamps used in PIDs are bulky and have relatively large power requirements.

Another problem in a PID is the interaction of the lamp with gases and structures in the ionization chamber of the PID. A typical ionization chamber is a cavity containing a pair of electrodes which are parts of the ion detector. The electrodes are typically made of a metal, and a high voltage (greater than 150 V) is applied across the electrodes to generate an electric field inside the ionization chamber. A gas sample enters the ionization chamber through a small gas inlet and leaves through a gas outlet. When organic gas molecules enter the ionization chamber, UV photons from the lamp ionize some of the organic gas molecules, and the electric field between the electrodes separates the resulting ions and electrons by attracting the ions and electrons to opposite polarity electrodes. An electrometer measures the resulting current. The magnitude of the measured current depends on the number of ions produced and therefore on the concentration of ionizable molecules in the sample and the intensity of UV light. If the light intensity is constant, the measured current can be converted to a concentration in part per million (ppm) of organic gas.

A concern in prior PIDs is contaminants introduced with the sample and metal atoms released from internal and external electrodes which can deposit on the optical window of the UV lamp and reduce the intensity of the UV light from the lamp. The coating reduces the sensitivity of the PID and requires recalibration of the PID using samples of known concentrations of detectable gas.

Conventional PIDs also suffers from unstable baseline currents because metallic electrodes which are exposed to high energy photons release free electrons which can produce a baseline current flow even when no ionizable gases are present. To calibrate the PID, the baseline current flow measured for a "zero gas" sample that contains no detectable molecules is stored and later used as a reference value. However, as the UV intensity decreases, the sensing electrodes release fewer electrons so that the previously stored baseline current is no longer valid. Frequent calibration of the detector with a "zero gas" is needed in order to re-establish a correct baseline current.

In addition, certain molecules such as water, methane, carbon monoxide, etc., which are referred to herein as interfering substances, have high ionization potentials and are not ionized but can block or absorb UV photons. When a gas sample being tested contains a large concentration of the interfering substances, some UV photons from the UV lamp are blocked or absorbed and prevented from ionizing detectable gas molecules. This effect decreases detector sensitivity in the presence of the interfering substances. This is a common problem of most PIDs. For example, the studies of Chilton, et al., *American Industrial Hygiene Association Journal*, 46:9–14 (1985) confirm that the response of a photo-ionization detector is markedly reduced in the presence of high water vapor concentration. U.S. Pat. No. 4,778,998 issued to Byron L. Carnahan, shows a method for humidity compensation in a PID, but the humidity compensation does not compensate for the UV intensity variation due to other interfering substances or contamination of the UV window.

Small gas detectors typically use diffusion to introduce a gas sample into the detector. The long diffusion time of gas molecules cause such gas detectors to have slow response to changes in surrounding gas concentrations. The problem is particularly severe for PIDs because most volatile organic gases have large molecular weight, and diffusion time is directly proportional to molecular weight. Some larger gas detectors can be equipped with optional sampling pumps that connect to inlets of the detectors. Such pumps are typically not suited for portable application because the attached sampling pumps are cumbersome and have relatively high energy consumption.

A PID is desired which is energy efficient, can be miniaturized for portable applications, does not require frequent calibrations, and has a quick response to changes in concentration of volatile gases in a surroundings.

SUMMARY OF THE INVENTION

A miniaturized ultraviolet (UV) lamp for a photo-ionization detector (PID) is energized by a pair of plates placed outside an envelope containing a gas and a driver circuit that controls power to the plates. This lamp is less complicated than conventional UV lamps because fabrication of metal electrodes inside a sealed envelope is not required. Accordingly, the UV lamp and a PID containing the UV lamp can be more easily miniaturized. The lamp structure is energy efficient because ionized gas in the envelop cannot conduct a current between the plates as is the case when plates are placed inside the envelop. Additionally, an energy efficient pulse width modulated driving method energizes the plates at a first level to initiate a glow discharge in the sealed envelop then reduces power to the plates while maintaining the glow discharge.

One embodiment of the invention provides a portable PID which is pocket size (including a battery) and capable of 12 hours of continuous operation. Such portable PIDs can be personal exposure devices that are carried or worn by users entering areas which may contain volatile gases. A warning such as a noise or a vibration from the PID can alert users when volatile gas concentrations in the surroundings exceed a programmable threshold level.

In accordance with another aspect of the invention, a UV shield is placed in front of a measurement electrode in an ionization chamber of a PID. The UV shield reduces the baseline current to nearly zero and reduces the need for frequent "zero gas" calibration.

In accordance with still another aspect of the invention, a UV monitor is placed inside the ionization chamber of the PID to monitor UV intensity; and the PID uses measured current and measured UV intensity when determining detectable gas concentrations. The PID automatically compensates for changes in UV intensity and requires fewer calibrations.

In accordance with still another aspect of the invention, a miniaturized sampling pump is built into the detector housing of a PID to provide a faster response to changes in the concentration of detectable molecules in the surroundings. Additionally, building the sampling pump into the detector housing provides an easy to carry package without a cumbersome pump attachment.

BRIEF DESCRIPTION OF THE DRAWINGS

Use of the same reference symbols in different figures indicates similar or identical items.

DESCRIPTION OF THE PREFERRED EMBODIMENT

Figure 1:
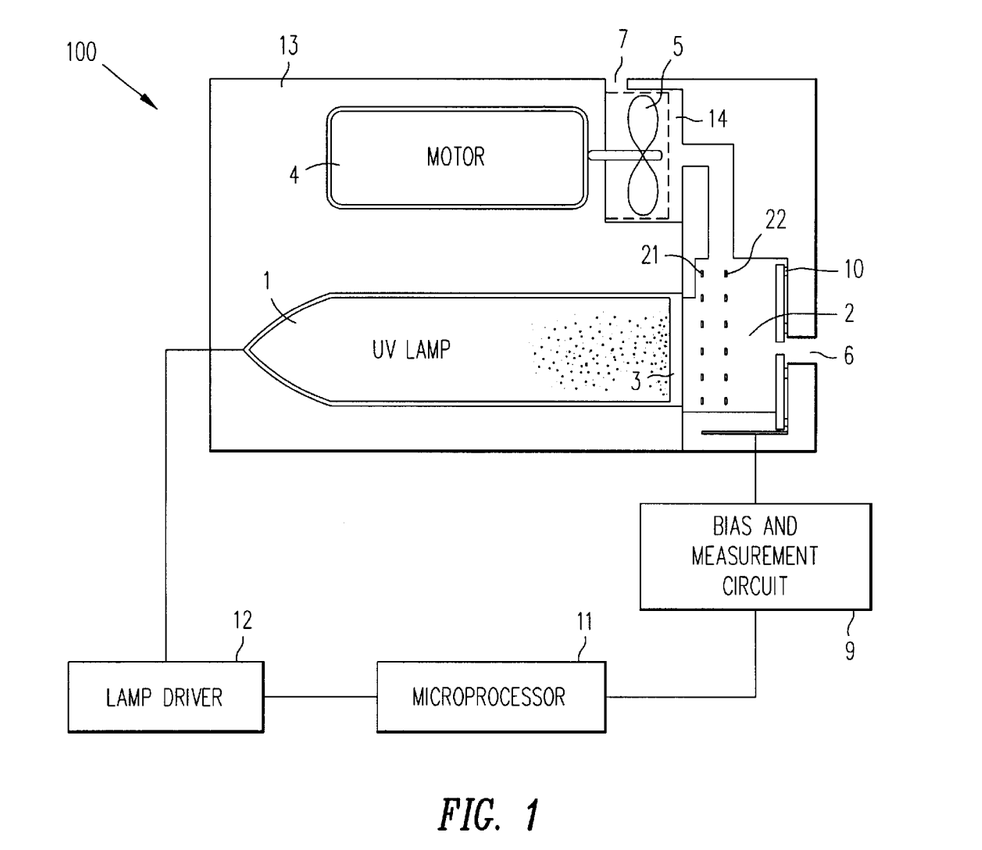
FIG. 1 shows a block diagram of a photo-ionization detector in accordance with an embodiment of the invention.

A photo-ionization detector (PID) in accordance with an embodiment of the invention can be miniaturized to pocket size for portable detection of volatile gases. To reduce the size and energy requirements of the PID, a number of innovations are employed including a simplified ultraviolet (UV) lamp structure. FIG. 1 shows a PID 100 which includes a UV lamp 1. UV lamp 1 radiates UV photons (light having wavelength less than about 150 nm) through an optical window 3 into an ionization chamber 2. A sampling pump 16, which is built into detector housing 13, contains a motor 4, an impeller 5, and a pump cavity 14 formed in detector housing 13. Centrifugal force generated by rotation of impeller 5 creates a vacuum near the center of impeller 5 which removes gas from ionization chamber 2. The gas removed from ionization chamber 2 is expelled through an outlet 7 as new sample gas is drawn into ionization chamber 2 through a gas inlet 6.

UV photons from lamp 1 ionize volatile gas molecules which are inside ionization chamber 2, and electrodes 21 and 22 inside ionization chamber 2 are biased to collect the resulting electrons and ions. A measurement circuit 9 provides bias voltages to electrodes 21 and 22 and measures electrical current caused by collection of ions at electrode 22. To distinguish the functions of electrodes 21 and 22, electrodes 21 and 22 are sometimes referred to herein as bias electrode 21 and measurement electrode 22. The current measured through measurement electrode 22 is referred to as the measurement current.

A microprocessor 11 receives from measurement circuit 9 a signal indicating the measurement current and a signal from a UV monitor 10 indicating the intensity of the UV light. UV monitor 10 is inside ionization chamber 2 behind electrodes 21 and 22 and measures the intensity of the UV light at a back wall of ionization chamber 2. Microprocessor 11 determines a concentration of volatile gas molecules from the measurement current and the measured UV intensity. From measured UV intensity, microprocessor 11 can detect and compensate for UV intensity variations when calculating the volatile gas concentration. Microprocessor 11 also controls lamp driver 12 and can increase or decrease lamp power to maintain UV intensity when a change in UV intensity is sensed.

Microprocessor 11 also executes firmware which provides a user interface for control of PID 100, display of volatile gas concentration, and generation of warning signals if volatile gas concentrations reach a threshold level. Controls, an alarm, and a LED display (not shown) provide a hardware portion of the user interface. A non-volatile memory (not shown) such as ROM, EEPROM, or Flash memory contains the firmware and parameters determined during calibration of PID 100 for use by microprocessor 11. A volatile memory (not shown) may also be required unless microprocessor 11 contains sufficient on-chip memory for execution of the firmware.

Figure 2:
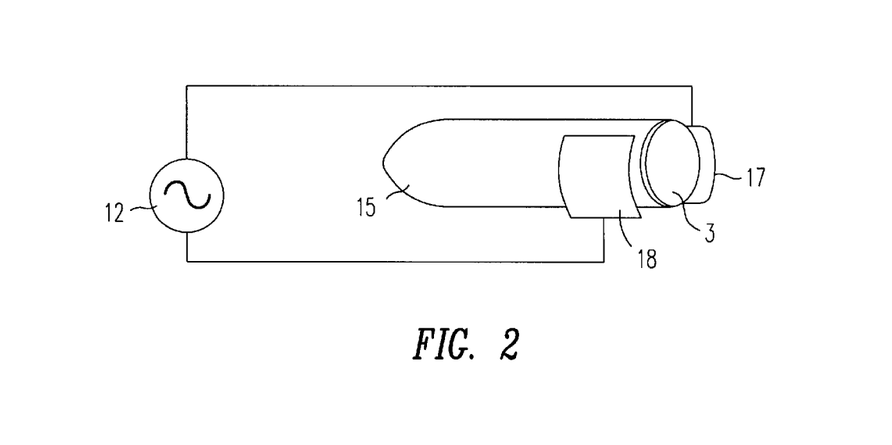
FIG. 2 shows a perspective view of a UV lamp having energizing plates outside a gas filled envelope.

FIG. 2 shows an embodiment of UV lamp 1. In the embodiment of FIG. 2, UV lamp 1 includes an envelope 15 which contains a mixture of gases such as argon, helium, hydrogen, and krypton. Outside envelope 15 are plates 17 and 18 which are connected to lamp driver circuit 12. Lamp driver circuit 12 applies a high voltage (about 800 V) AC signal to plates 17 and 18 which creates a strong electric field that ionizes gas molecules inside envelope 15. The electrons and ions inside envelope 15 recombine to generate UV photons in a process known as glow discharge. Optical window 3 is formed at one end of envelop 15 and is made of a material which passes UV photons having desired energies.

Figure 3:
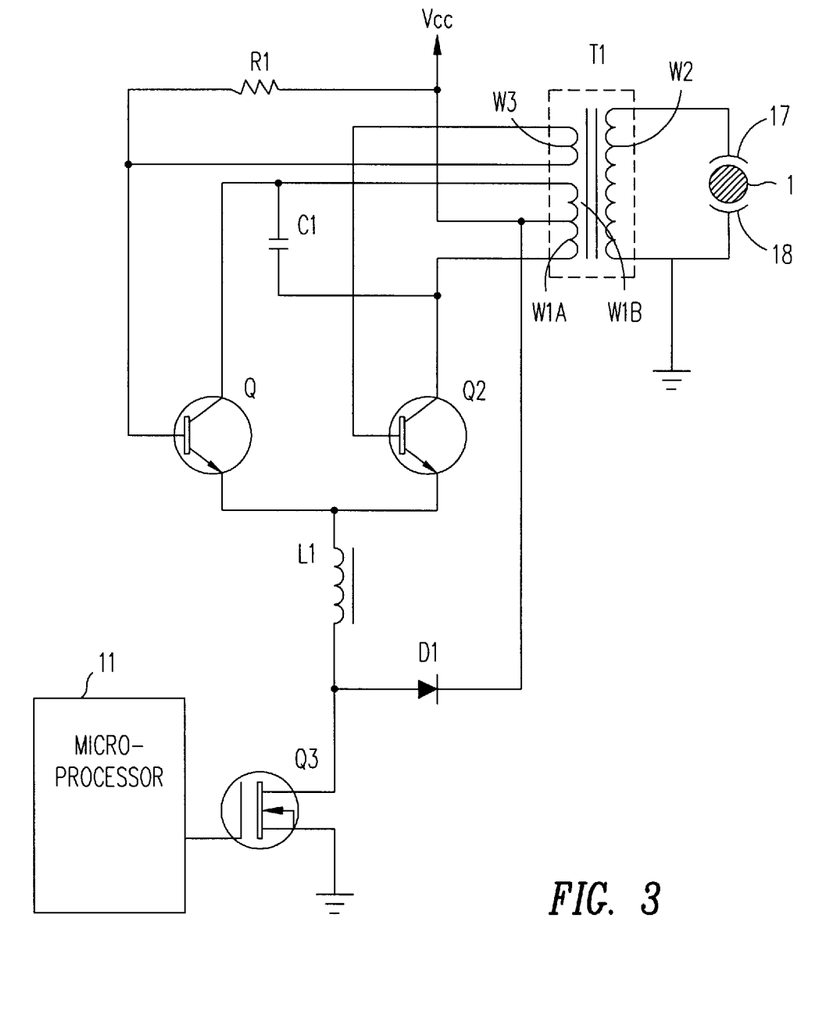
FIG. 3 is a schematic of a UV lamp and driver circuit in accordance with an embodiment of the invention.

FIG. 3 shows a schematic of an embodiment of lamp driver circuit 12 which generates a high voltage AC signal across plates 17 and 18. In the embodiment of FIG. 3, a self-oscillating circuit generates the high voltage AC signal at a secondary winding W2 of a transform T1. To begin oscillations, an inductor L1 is energized by a current from a supply voltage Vcc through a primary winding W1 of transformer T1 and a transistor Q1 or Q2 to inductor L1 and from inductor L1 through a transistor Q3 to ground. Once inductor L1 is energized, inductor L1 maintains current through a diode D1 to a tap in primary winding W1.

The current from inductor L1 or from supply voltage Vcc to the tap in the primary winding flows through either a first part W1A or a second part W1B of primary winding W1, depending on whether transistor Q1 or transistor Q2 conducts. The senses of currents through windings W1A and W1B are opposite and induce opposite polarity voltage in secondary winding W2 and a feedback winding W3. Feedback winding W3 provides a current between the bases of transistors Q1 and Q2 that determines which of transistors Q1 and Q2 conducts. The base of transistor Q1 is also connected through a resistor R1 to a supply voltage Vcc so that if feedback winding W3 does not carry a current then transistor Q1 conducts.

Oscillations occur because increasing current through winding W1A when transistor Q1 is turned on induces a current in feedback winding W3 that shuts off transistor Q1 and turns on transistor Q2. When transistor Q2 is turned on, increasing current through winding W1B reverses current through feedback winding W3, shuts off transistor Q2, and turns on transistor Q1. Transistors Q1 and Q2 thus turn on and off cyclically 180° out of phase with each other, and the resulting changes in currents through windings W1A and W1B induce the AC voltage in winding W2 which is applied to plates 17 and 18. A capacitor C1 connected between the bases of transistors Q1 and Q2 determines how quickly transistors Q1 and Q2 turn off and on and therefore controls the frequency of oscillation. In one embodiment of the invention, capacitor C1 and windings W1A, W1B, and W2 of transformer T1 are selected to produce a high voltage AC signal (>800 V) which oscillates at about 100 kHz from the supply voltage Vcc (about 5 V). For example, in one embodiment of the invention, turns in windings W1A, W1B, W2, and W3 are in the proportions 1:1:130:1.

During operation of PID 100, microprocessor 11 generates a series of pulses which turn transistor Q3 on and off. When transistor Q3 is on, supply voltage Vcc drives a current through winding W1A or W1B and inductor L1. When transistor Q3 is turned off, energy stored in inductor L1 sustains the high voltage AC signal until the energy stored in inductor L1 is exhausted or transistor Q3 is turned on again. The amplitude of the AC signal falls as energy stored in inductor L1 is consumed. In accordance with an aspect of the invention, pulse-width modulation by microprocessor 11 changes the amount of energy stored in inductor L1 and therefore the energy delivered to UV lamp 1 through transformer T1. Longer pulses transfer more power. Short pulses transfer less. Microprocessor 11 can adjust pulse width of the signal applied to the gate of transistor Q3 to keep the UV intensity at a desired level.

In accordance with another aspect of the invention, microprocessor 11 selects a pulse width which minimize energy consumed by UV lamp 1. In a typical gas discharge lamp, the AC voltage required to start glow discharge is usually higher (10 to 20% more) than the voltage required to sustain the glow discharge. With the pulse width modulated driver circuit 12, microprocessor 11 can start UV lamp 1 using more power (higher AC voltage) and then decrease the power (lower the voltage level) to sustain the glow discharge. For example, pulse width and the power can be reduced a fixed delay time after glow discharge begins.

Another energy saving feature of UV lamp 1 is the that plates 17 and 18 are insulated from the ions and electrons inside envelope 15 during the glow discharge. Accordingly, no DC current flows between plate 17 and plate 18, and initiating and sustaining the glow discharge does not suffer from energy loss due to DC current. Miniaturization of UV lamp 1 and envelope 15 also saves power because smaller gas volumes require less energy to initiate and sustain the glow discharge. Envelope 15 is easily miniaturized because no electrodes or other devices are required inside envelope 15, and total power consumed by lamp driver 12 and UV lamp 1 can be less than 100 mW.

Figure 4:
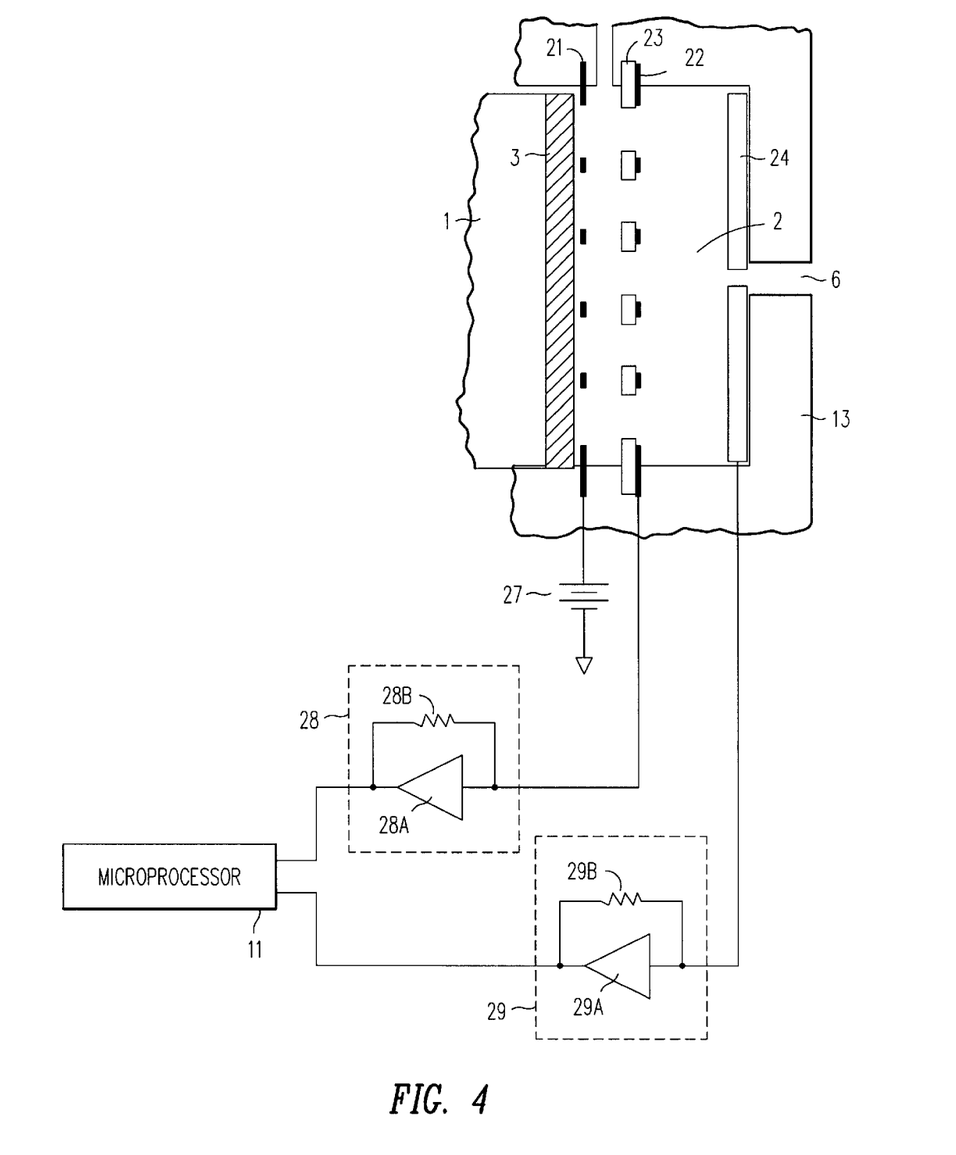
FIG. 4 shows a cross-sectional view of an ionization chamber for the photo-ionization detector of FIG. 1.

FIG. 4 shows an embodiment of ionization chamber 2. Optical window 3 of UV lamp 1 is disposed at a front wall of ionization chamber 2. Electrodes 21 and 22 are placed parallel to each other inside ionization chamber 2. A UV shield 23 is placed between electrodes 21 and 22. In one embodiment of the invention, UV shield 23 is made of a sheet of material which is inert to gas and ions generated in ionization chamber 2, provides high electrical insulation, and is opaque to the high energy UV light. Alternatively, a coating such as a photo-resist material commonly employed in integrated circuit manufacture, can be deposited (or coated) on one side of measurement electrode 22 to form UV shield 23. The photo-resist prevent UV photons from reaching the exposed metallic surface of measurement electrode 22, while ions pass through openings in measurement electrode 22 for collection by measure electrode 22.

Bias electrode 21 is connected to a high voltage DC source 27 which provides a DC voltage greater than about 150 V. Bias electrode 21 repels positive ions formed when UV photons hits ionizable gas molecules. UV photons striking electrode 21 can liberated electrons from electrode 21 but those electrons are typically attracted back to electrode 21 and do not contribute to a baseline current between electrodes 21 and 22.

Measurement electrode 22 is near ground voltage and separated from bias electrode 21 to create an electric field between electrodes 21 and 22. UV shield 23 is disposed between measurement electrode 22 and UV lamp 1 so that UV photons cannot strike measurement electrode 22 and liberate electrons, but openings through UV shield 23 permit passage of positive ions toward measurement electrode 22 and electrons toward bias electrode 21. Shielding of electrode 22 reduces baseline current because electrons liberated from measurement electrode 22 would be attracted to bias electrode 21 thereby increasing the baseline current and reducing the signal-to-noise ratio for the measurement current.

A third electrode 24 which is part of UV monitor 10 is placed behind electrodes 21 and 22. Electrode 24 monitors the intensity of UV light and is sometimes referred to herein as monitor electrode 24. Monitor electrode 24 is made of UV sensitive material such as a metal. UV photons from lamp 1 which strike monitor electrode 24 liberate electrons which are attracted to bias electrode 21. The current from monitor electrode 24 provides an indication of the intensity of UV radiation from lamp 1 and is some times referred to herein as the monitor current.

Measurement electrode 22 and monitor electrode 24 are respectively connected to electrometers 28 and 29, which in one embodiment are simply a current-to-voltage converters formed from a low leakage operational amplifiers 28A and 29A and high feedback resistors 28B and 29B. Electrometers 28 and 29 provide to microprocessor 11 analog signals respectively indicating the measurement current and the monitor current. Microprocessor 11 converts the analog signals to digital values. Alternatively, analog-to-digital converters may be required between microprocessor 11 and electrometers 28 and 29 if microprocessor 11 cannot accept analog signals.

Microprocessor 11 receives from electrometers 28 and 29 the signals indicating the measurement and monitor currents and implements procedures necessary for detecting variations in the UV light intensity and determining a concentration of volatile gases. The source of the variations in UV light can be changes in the electrical performance of lamp 1, contaminants on UV optical window 3, interfering substances in the gas sample, or an unknown cause. Microprocessor 11 compensates for variations, whatever the cause, by adjusting the UV lamp intensity (energy output from driver circuit 12) and/or applying an intensity correction factor when determining volatile gas concentrations.

PID 100 is initialized or calibrated for operation using two calibration steps, a "zero gas" calibration and a known sample calibration. A user can place PID 100 in zero gas calibration mode using the user interface. During zero gas calibration, a clean dry air sample which contains no ionizable volatile gases and no interfering substances such as methane, water vapor, or dust particles passes through ionization chamber 2. The signal from electrometer 28 to microprocessor 11 indicates a measurement current that should be very close to zero because the sample contains no ionizable gases and UV shield 23 shields measurement electrode 22 from UV photons which would free electrons and create a baseline current. The very small measurement current provides a baseline reading which should stay small even if the UV intensity changes over time. UV shield 23 being in front of measurement electrode 22 thus stabilizes the baseline reading for the PID. Microprocessor 11 stores the baseline reading in non-volatile memory for later use.

Zero gas calibration also provides a reference level for the monitor current. UV monitor 10 detects photons from UV lamp 1 which pass through the holes in UV shield 23 and reach monitor electrode 24 without ionizing a volatile gas molecule or being absorbed by interfering substances. UV photons striking the metal surface of monitor electrode 24 free electrons which create a monitor current by flowing from monitor electrode 24 to bias electrode 21, and when no ions are formed in ionization cavity 2, the monitor current is proportional to the intensity of UV light reaching monitor electrode 24. Microprocessor 11 stores the monitor current for the zero gas sample to establish a reference value to which subsequent monitor currents are compared to detect changes in UV intensity.

The user can also calibrate PID 100 with a sample having a known concentration of volatile gas molecules. When the known sample is introduced into ionization chamber 2, resulting measurement and monitor currents are observed. Assuming UV intensity is constant and sufficiently high, the volatile gas molecule concentration is approximately proportional to the part of the measurement current due to collection of ions. During known sample calibration, microprocessor 11 determines a proportionality constant which is the ratio of the known concentration to difference between the measured current and the baseline current. The proportionality constant is saved in non-volatile memory at the end of the calibration and is subsequently used in determining volatile gas concentrations.

As described above, during normal operation of a PID, the UV intensity gradually drops due to contaminants such as metal atoms, oil film, or dust particles which deposit on optical window 3 over a period of time. In the embodiment of FIG. 1, metal atoms are not deposited on the inside surface of UV lamp 1 because plates 17 and 18, being outside envelope 15, are not subject to bombardment by ions and electrons during a glow discharge process which may free metal atoms. However, in other systems, metal could deposit on surfaces inside a lamp if metal electrodes are in a sealed envelope with gases in glow discharge.

Another cause of changes in UV intensity is varying amounts of interfering substances such as water, methane, or other non-ionizable gas molecules or suspended particles, which block some UV photons in ionization chamber 2. Microprocessor 11 identifies a change in UV intensity from the monitor current and compensates for the change by changing energy output from lamp driver circuit 12 or by changing a correction factor used when determining a volatile gas concentration from the measurement current.

Measurement electrode 22 and monitor electrode 24 are at similar potentials (near ground) so that each of electrodes 22 and 24 collects some of the positive ions formed inside ionization chamber 2. Accordingly, both the measurement current and the monitor current increase when ionizable gas molecules are present. When this occurs, the monitor current is no longer proportional to the UV intensity because the monitor current has a contribution due to ionized molecules. Accordingly, microprocessor 11 cannot use a simple proportionality to the monitor current when determining UV intensity if the ionization chamber 2 contains a high concentrations of volatile gas molecules.

Microprocessor 11 can use a previous reading of the monitor current obtained when the measurement current was small and ignore the latest reading of the monitor current obtained when the measurement current is large. A value for the monitor current is periodically stored when the measurement current is small and used when the measurement current is relatively large. Since the UV intensity does not change drastically during a short period of time, this UV intensity monitoring and compensation is adequate for most applications.

The alternative technique is for microprocessor 11 determine the UV intensity using the monitor current reduced by an amount proportional to the measurement current. Assuming that electrometers 28 and 29 have identical responses, the proportionality constant for reduction of the monitor current depends on the ratio of percentage of ions collected by monitor electrode 24 to the percentage of ions collected by measurement electrode 22 and should be a constant which depends on the geometry of ionization chamber 2 and the flow rate through ionization chamber 2. If the spacing between electrodes 21, 22, and 24 and the relative sizes of measurement and monitor electrodes 22 and 24 are properly selected, the percentage of ions collected by measurement electrode 22 is approximately equal to the percentage of ions collected by monitor electrode 24, and microprocessor 11 can determine the UV intensity at monitor electrode 24 by subtracting the measurement current from the monitor current to separate the portion of the monitor current which is due to UV photons striking monitor electrode 24. Alternatively, a differential amplifier connected to electrometers 28 and 29 can provide a signal proportional to the difference between the measurement and monitor currents.

Figure 5:
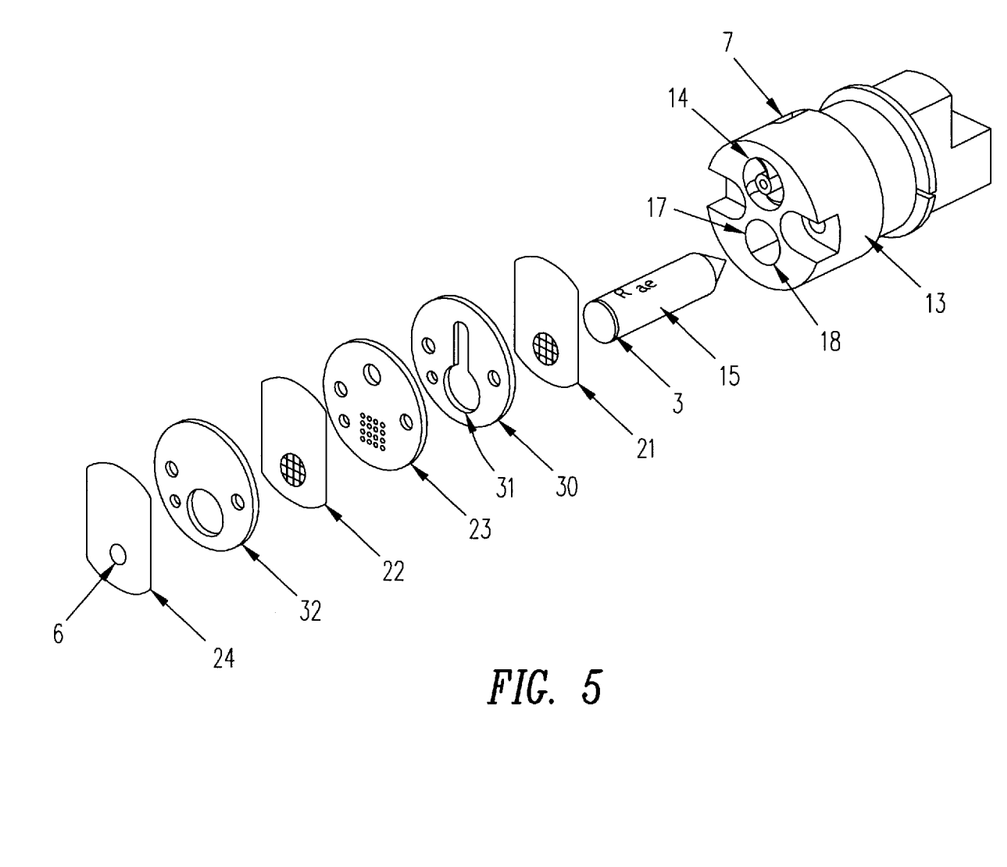
FIG. 5 is an expanded perspective drawing of a detector housing and an ionization chamber of a photo-ionization detector in accordance with an embodiment of the invention.

FIG. 5 shows an expanded perspective drawing of components in an exemplary embodiment of PID 100. In the exemplary embodiment, PID 100 is a pocket size PID which measures 1.75" W×6.0" L,×1.0" H and weights 6.4 ounces including two AA size Ni-Cd batteries (not shown) which provide power for 12 hours of continuous operation. UV lamp 1 includes envelope 15 which is 0.25" in diameter and 1.1" in length and filled with 30% argon, 50% helium, and 20% krypton at about 25 Torr. Optical window 3 is made of crystalline magnesium fluoride and transmits 10.6 eV photons, and the remainder of envelope 15 is glass. Plates 17 and 18 are copper and measure 0.20" by 0.20", and driver circuit 12 provides an AC voltage at about 100 kHz and 800 V peak-to-peak to energize UV lamp 1.

Sampling pump 16 is contained in detector housing 13 and measures 0.8" in diameter and 1.5" in length. In sampling pump 16, impeller 5 is 0.3 inches in diameter and has four blades having a pitch of about 30°; and motor 4 is a 5 V DC motor part No. 707L61 available from Portescap US, Inc. of Haupage, N.Y. which consumes 25 mW of power when turning impeller 5 at a rate of 10,000 rpm to provide a flow rate of 50 cc per minute through ionization chamber 2.

Microprocessor 11 is a 68HC11 microprocessor which is commercially available from Motorola Inc and is connected to a 32 kbyte EEPROM and a 512 byte RAM. The EEPROM contains constants determined during calibration and firmware executed by microprocessor 11 to implement user interface, calibration, power control, and volatile gas concentration calculation functions.

Ionization chamber 2 is made of stainless steel electrodes 21, 22, and 24 and Teflon spacers 30, 23, and 32 layered as shown in FIG. 5 to form a 20 microliter ionization chamber 2. Bias electrode 21 is a stainless steel sheet having a mesh or grid etched in at a position which places the mesh inside ionization chamber 2 adjacent optical window 3. Centers of openings in the grid in bias electrode 21 are about 0.050" apart while strips forming the grid are about 0.010" wide. A Teflon spacer 30 which is 0.040" thick and adjacent bias electrode 21 has a hole 31 that forms a portion of ionization chamber 2 and an air duct from ionization chamber 2 to pump cavity 14. A 0.25" diameter circular portion of hole 31 in spacer 30 defines the volume of ionization chamber 2. UV shield 23 is formed from a Teflon sheet 0.020" thick and is adjacent spacer 30. Rows and columns of small holes formed in UV shield 23 allow the UV light and gas molecules to pass through UV shield 23. The spacing of holes in UV shield 23 is identical to the grid spacing on bias electrode 21, i.e. 0.050".

Measurement electrode 22 is identical to bias electrode 21 and includes a grid etched from a stainless steel sheet. Spacer 30 and UV shield 23 are between measurement electrode 22 and bias electrode 21 so that measurement and bias electrodes are separated by about 0.06". Measurement electrode 22 is placed behind UV shield 23 with the grid in measurement electrode 22 aligned with the hole pattern in UV shield 23 so that the grid is hidden behind UV shield 23 as shown in FIG. 4. UV shield 23 stops high energy UV photons from reaching measurement electrode 22 but still allows ions, electrons, and UV photons to pass through holes in UV shield 23.

A Teflon spacer 32 which is about 0.10" thick separates measurement electrode 22 from monitor electrode 24. A 0.05" hole or inlet 6 through monitor electrode 24 permits gas flow into ionization chamber 2 and reduces the area of monitor electrode 6 which is available for collecting ions. The size of the inlet 6 and the separation between measurement electrode 22 and monitor electrode 24 can be adjusted to control the fraction of ions collected by each electrode 22 and 24.

Figure 6:
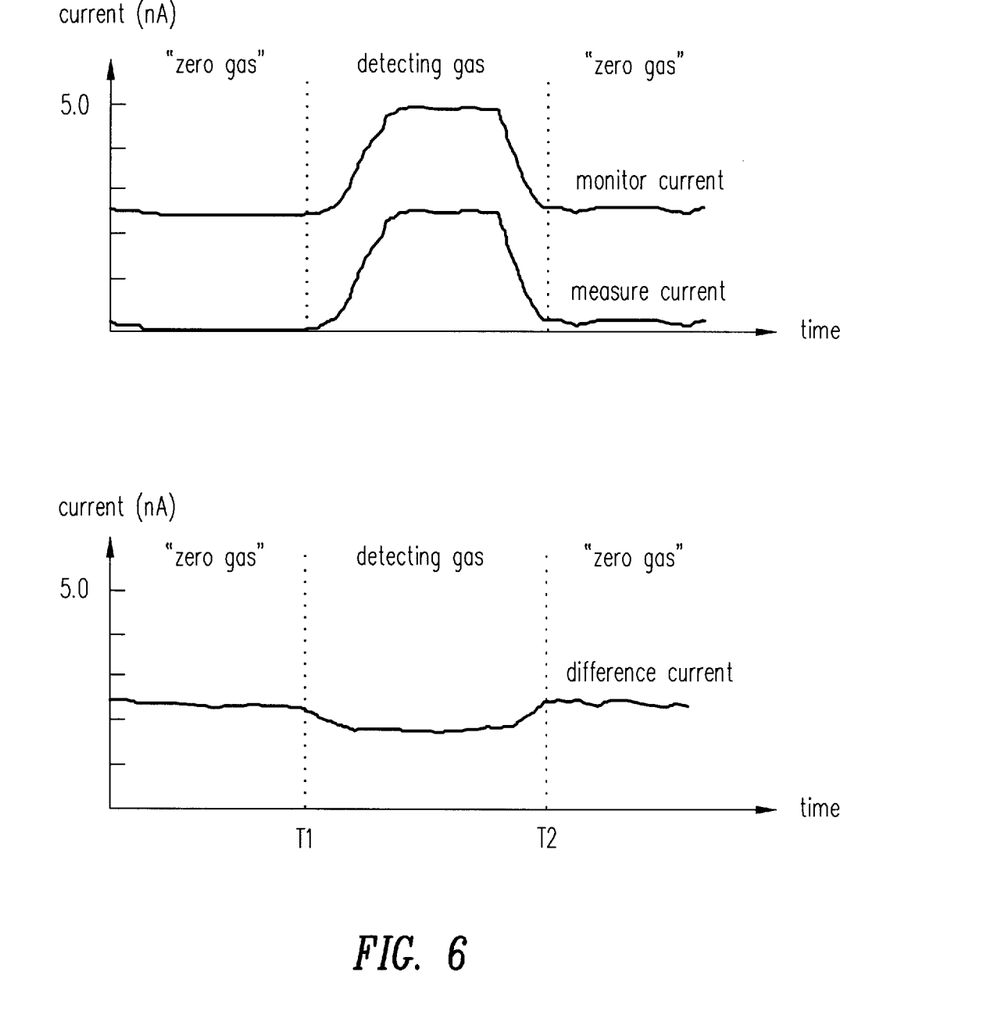
FIG. 6 is an example of the currents through monitor and measurement electrodes in an embodiment of the invention.

FIG. 6 shows example plots of the monitor current, measurement current, and difference between the two in the exemplary embodiment. From time T0 to T1, when no detectable gas is in the sample (i.e. "zero gas" condition), the difference between the monitor current and the measurement current is fixed at about 2.5 nA. Between time T1 and T2, when detectable gas is introduced to the sample, both the monitor and measurement currents increase. The difference between the measurement current and the monitor current drops slightly to about 2.0 nA because ionizable (and non-ionizable) gas molecules in the sample block some UV photons and reduce the number of UV photons reaching the monitor electrode. However, the differential signal indicates the UV intensity reaching the monitor electrode and can be used when compensating for decreased UV intensity.

In an alternative embodiment, UV monitor 10 is a UV sensor which is not disturbed by volatile gas ions, and the output of UV monitor 10 is used directly for UV intensity compensation without regard for the measurement current. Suitable UV sensors are available from Hamamatsu Inc. With each of the above techniques, microprocessor 11 monitors and compensates for the UV intensity variation due to UV lamp contamination and external interfering substances. The result is a PID with a more stable and accurate reading of volatile gas concentration.

Although the present invention has been described with reference to particular embodiments, the description is only an example of the invention's application and should not be taken as a limitation. Various adaptations and combinations of features of the embodiments disclosed are within the scope of the invention as defined by the following claims.

I claim:

1. A photo-ionization detector comprising:
    a detector housing having an ionization chamber formed therein, the detector hosing including a block that forms a wall of the ionization chamber;
    a pump disposed within the block to create a flow of gases from a surrounding environment through the ionization chamber;
    an ultraviolet lamp disposed within the block and positioned to transmit ultraviolet light into the ionization chamber; and
    an ion detector at least partially disposed inside the ionization chamber.

2. The photo-ionization detector of claim 1, wherein the photo-ionization detector is small enough to be carried by a user for detection of personal exposure to volatile gases.

3. The photo-ionization detector of claim 1, wherein the ultraviolet lamp comprises:
    a sealed envelope enclosing a quantity of gas, the sealed envelope including an optical window which is transparent to a desired frequency of ultraviolet light and positioned adjacent to the ionization chamber; and
    a pair of plates which are electrically insulated from each other and placed outside the sealed envelope to provide an electric field which induces a glow discharge process within the envelope.

4. The photo-ionization detector of claim 1, further comprising a battery capable of powering the photo-ionization detector.

5. The photo-ionization detector of claim 1, wherein the ion detector comprises an electrode which is biased to attract positive ions, and the photo-ionization detector further comprises a shield that prevents ultraviolet light from striking the electrode.

6. The photo-ionization detector of claim 1, wherein the detector housing further comprises:
    a first electrode which is adjacent the block and is a part of the ion detector, wherein the first electrode includes a grid which is aligned with the ultraviolet lamp;
    a spacer adjacent the first electrode, the spacer having a hole formed therethrough, wherein the hole is aligned with the grid and defines boundaries of the ionization chamber; and
    a second electrode which is adjacent the spacer and is part of the ion detector, wherein the second electrode includes a second grid which is aligned with the ultraviolet lamp.

7. The photo-ionization detector of claim 6, wherein the detector housing further comprises a shield disposed between the second electrode and the ultraviolet lamp to stop ultraviolet light from striking the second electrode.

8. A photo-ionization detector comprising:

a detector housing having an ionization chamber formed therein;

a pump integrated into the detector housing to create a flow of gases from a surrounding environment through the ionization chamber;

an ultraviolet lamp disposed within the detector housing and positioned to transmit ultraviolet light into the ionization chamber;

an ion detector at least partially disposed inside the ionization chamber;

an ultraviolet intensity monitor disposed within the ionization chamber; and a measuring circuit coupled to the ion detector and the ultraviolet intensity monitor, wherein the measuring circuit generates a signal representing a concentration of ionizable gas within the ionization chamber.

9. A photo-ionization detector comprising:

an ionization chamber:

an ultraviolet lamp positioned to transmit ultraviolet light into the ionization chamber;

an ion detector at least partially disposed inside the ionization chamber, wherein the ion detector comprises an electrode which is biased to attract positive ions; and a shield that prevents ultraviolet light from striking the electrode, wherein the shield comprises a layer of photo-resist formed on the electrode.

10. A photo-ionization detector comprising:

an ionization chamber;

an ultraviolet lamp positioned to transmit ultraviolet light into the ionization chamber;

an ion detector at least partially disposed inside the ionization chamber, wherein the ion detector comprises an electrode which is biased to attract positive ions; and a shield that prevents ultraviolet light from striking the electrode, wherein the shield comprises an opaque sheet formed in a pattern that matches the electrode in shape.

11. A photo-ionization detector comprising:

an ionization chamber;

an ultraviolet lamp positioned to transmit ultraviolet light into the ionization chamber;

a first electrode and a second electrode disposed in the ionization chamber, wherein the first electrode is electrically biased to attract negatively charged particles, and the second electrode is electrically biased to attract positively charged particles; and a shield positioned on the second electrode to prevent ultraviolet light generated by the ultraviolet lamp from striking the second electrode.

12. The photo-ionization detector of claim 11, further comprising an electrometer coupled to the second electrode, wherein the electrometer measures a current through the second electrode.

13. The photo-ionization detector of claim 12, further comprising means for using the current measured by the electrometer to determine a concentration of ionizable gas molecules in the ionization chamber.

14. The photo-ionization detector of claim 11, wherein the shield comprises a layer of photo-resist formed on the second electrode.

15. The photo-ionization detector of claim 11, wherein the shield comprises an opaque sheet formed in a pattern that matches the second electrode in shape.

16. A photo-ionization detector comprising:

an ionization chamber;

an ultraviolet lamp positioned to transmit ultraviolet light into the ionization chamber;

an ultraviolet intensity detector positioned to detect an intensity of ultraviolet light in the ionization chamber;

a first electrode and a second electrode disposed in the ionization chamber, wherein the first electrode is electrically biased to attract negatively charged particles, and the second electrode is electrically biased to attract positively charged particles; and a shield positioned to prevent ultraviolet light generated by the ultraviolet lamp from striking the second electrode.

17. The photo-ionization detector of claim 16, wherein the ultraviolet intensity detector comprises a third electrode disposed in a path of ultraviolet light in the ionization chamber, wherein the third electrode is biased to attract positively charged particles.

18. The photo-ionization detector of claim 17, further comprising:

a first electrometer coupled to measure a first current through the second electrode; and a second electrometer coupled to measure a second current through the third electrode.

19. The photo-ionization detector of claim 18, further comprising means for using the first and second currents to determine a concentration of ionizable gas molecules in the ionization chamber.

20. The photo-ionization detector of claim 18, further comprising a microprocessor coupled to the first and second electrometers, wherein the microprocessor uses levels of the first and second currents to determine a concentration of ionizable gas molecules in the ionization chamber.

21. The photo-ionization detector of claim 20, wherein the microprocessor uses the first and second currents to determine the ultraviolet intensity in the ionization chamber.

22. The photo-ionization detector of claim 21, wherein the microprocessor is coupled to the ultraviolet lamp and changes a power level of the ultraviolet lamp to compensate for changes in the ultraviolet intensity.

23. A photo-ionization detector comprising:

an ionization chamber;

an ultraviolet lamp positioned to transmit ultraviolet light into the ionization chamber;

a measurement electrode biased to collect ions formed in the ionization chamber;

an ultraviolet sensor placed inside the ionization chamber; and measuring circuitry coupled to receive readings from the measurement electrode and the ultraviolet sensor.

24. The photo-ionization detector of claim 23, wherein the measuring circuitry is coupled to the ultraviolet lamp and adjusts power supplied to the ultraviolet lamp to compensate for changes in a reading from the ultraviolet sensor.

25. The photo-ionization detector of claim 23, wherein the measuring circuitry detects a current through the measurement electrode and determine a concentration of ionizable gas in the ionization chamber using the detected current and a reading from the ultraviolet sensor.

* * * * *